United States Patent
Lovell (10) Patent No.: US 6,631,718 B1
(45) Date of Patent: Oct. 14, 2003

(54) AIR MASK WITH SEAL (75) Inventor: John R. Lovell, Manchester, NH (US)

(73) Assignee: SleepNet Corporation, Manchester, NH (US)

( * ) Notice: Subject to any disclaimer, the term of this patent is extended or adjusted under 35 U.S.C. 154(b) by 0 days.

(21) Appl. No.: 09/328,027

(22) Filed: Jun. 8, 1999

(51) Int. Cl.$^7$ .............................................. A62B 18/08
(52) U.S. Cl. ............................ 128/206.24; 128/207.13
(58) Field of Search ....................... 128/206.21, 206.23, 128/206.24, 206.25, 206.14, 206.26, 201.18, 848, 206.12, 206.13, 206.18, 206.27, 206.28, 207.13; 2/430

(56) References Cited

U.S. PATENT DOCUMENTS

| | | | |
|---|---|---|---|
| 428,592 | A | 5/1890 | Chapman |
| 1,206,045 | A | 11/1916 | Smith |

(List continued on next page.)

FOREIGN PATENT DOCUMENTS

| | | |
|---|---|---|
| CA | 618807 | 4/1961 |
| CA | 623129 | 7/1961 |
| DE | 195 48 380 | 7/1996 |
| DE | 42 12 259 | 1/1998 |
| DE | 198 07 961 | 8/1999 |
| EP | 0 549 299 A2 | 6/1993 |
| EP | 0 747 078 A2 | 12/1996 |
| EP | 0 747 078 | 12/1996 |
| FR | 780018 | 4/1935 |
| FR | 2 720 280 | 12/1995 |
| FR | 2 749 176 | 12/1997 |
| WO | WO 93/24169 | 12/1993 |
| WO | WO 97/09090 | 3/1997 |
| WO | WO 98/18514 | 5/1998 |
| WO | WO 98/48878 | 11/1998 |
| WO | WO 99/43375 | 9/1999 |
| WO | WO 99/58181 | 11/1999 |

OTHER PUBLICATIONS

Healthdyne® Technologies Soft Series™ Mask advertisement, 1 page, undated.
Medical Industries America Universal Deluxe C.P.A.P. Headgear advertisement, 1 page, undated.
Puritan Bennett Companion® Nasal CPAP Masks advertisement, 1 page, undated.
American Society for Testing and Materials (ASTM) "Designation D 2240–97ϵ1: Standard Test Method for Rubber Property—Durometer Hardness", approved Feb. 10, 1997, undated Feb., 1999 (pp. 1–4).
Barracuda The Best Swin Goggles Packaging (date unknown), 1 page.

(List continued on next page.)

Primary Examiner—Weilun Lo
Assistant Examiner—Teena Mitchell
(74) Attorney, Agent, or Firm—Testa, Hurwitz & Thibeault, LLP (57) ABSTRACT A nasal mask includes a flexible shell and a seal. The flexible shell has an inlet and includes a malleable element disposed about a periphery of the shell for maintaining the shell in a user selectable configuration. The seal is disposed along a perimeter of the shell so as to form a chamber within the shell when the mask is donned by a user.

17 Claims, 11 Drawing Sheets

U.S. PATENT DOCUMENTS

| | | | |
|---|---|---|---|
| 1,610,793 A | 12/1926 | Kaufman | |
| 1,632,449 A | 6/1927 | McKesson | |
| 2,248,477 A | 7/1941 | Lombard | |
| 2,254,854 A | 9/1941 | O'Connell | |
| 2,376,871 A | 5/1945 | Fink | |
| D156,060 S | 11/1949 | Wade | |
| D161,337 S | 12/1950 | Hill | |
| 2,540,567 A | 2/1951 | Bennett | |
| 2,625,155 A | 1/1953 | Engelder | |
| 2,693,178 A | 11/1954 | Gilroy | |
| 2,837,090 A | 6/1958 | Bloom et al. | |
| 2,868,196 A | 1/1959 | Stampe | |
| 2,902,033 A | 9/1959 | Galleher, Jr. | |
| 2,917,045 A | 12/1959 | Schildknecht et al. | |
| 2,931,356 A | 4/1960 | Schwarz | |
| 3,042,035 A | 7/1962 | Coanda | |
| 3,117,574 A | 1/1964 | Replogle | |
| 3,288,138 A | 11/1966 | Sachs | |
| 3,315,672 A | 4/1967 | Cunningham et al. | |
| 3,330,273 A | 7/1967 | Bennett | |
| 3,725,953 A | 4/1973 | Johnson et al. | |
| 4,062,357 A | 12/1977 | Laerdal | |
| D248,497 S | 7/1978 | Slosek | |
| 4,167,185 A | 9/1979 | Lewis | |
| 4,201,205 A | 5/1980 | Bartholomew | |
| 4,226,234 A | 10/1980 | Gunderson | |
| 4,231,363 A | 11/1980 | Grimes | |
| 4,266,540 A | 5/1981 | Panzik et al. | |
| 4,337,767 A | 7/1982 | Yahata | |
| 4,354,488 A | 10/1982 | Bartos | |
| 4,369,284 A | 1/1983 | Chen | |
| 4,412,537 A | 11/1983 | Tiger | |
| 4,414,973 A | 11/1983 | Matheson et al. | |
| 4,417,575 A | 11/1983 | Hilton et al. | |
| 4,446,576 A | 5/1984 | Hisataka | |
| 4,454,880 A | 6/1984 | Muto et al. | |
| 4,458,679 A | 7/1984 | Ward | |
| 4,572,323 A | 2/1986 | Randall | |
| 4,593,688 A | 6/1986 | Payton | |
| D285,496 S | 9/1986 | Berman | |
| 4,665,570 A * | 5/1987 | Davis | 2/428 |
| 4,674,134 A | 6/1987 | Lundin | |
| 4,707,863 A | 11/1987 | McNeal | |
| 4,770,169 A | 9/1988 | Schmoegner et al. | |
| 4,782,832 A | 11/1988 | Trimble et al. | |
| 4,799,477 A | 1/1989 | Lewis | |
| 4,807,617 A | 2/1989 | Nesti | |
| 4,811,730 A | 3/1989 | Milano | |
| 4,856,118 A | 8/1989 | Sapiejewski | |
| D304,384 S | 10/1989 | Derobert | |
| 4,915,106 A | 4/1990 | Aulgur et al. | |
| 4,944,310 A | 7/1990 | Sullivan | |
| D310,431 S | 9/1990 | Bellm | |
| 4,960,121 A | 10/1990 | Nelson et al. | |
| 4,971,051 A | 11/1990 | Toffolon | |
| 4,989,271 A | 2/1991 | Sapiejewski et al. | |
| 5,003,631 A | 4/1991 | Richardson | |
| 5,003,633 A | 4/1991 | Itoh | |
| 5,018,519 A | 5/1991 | Brown | |
| 5,074,297 A | 12/1991 | Venegas | |
| 5,093,940 A | 3/1992 | Nishiyama | |
| 5,109,839 A | 5/1992 | Blasdell et al. | |
| 5,138,722 A | 8/1992 | Urella et al. | |
| 5,146,914 A | 9/1992 | Sturrock | |
| 5,181,506 A | 1/1993 | Tardiff, Jr. et al. | |
| 5,199,424 A | 4/1993 | Sullivan et al. | |
| D335,322 S | 5/1993 | Jones | |
| 5,243,971 A | 9/1993 | Sullivan et al. | |
| 5,245,995 A | 9/1993 | Sullivan et al. | |
| 5,269,296 A | 12/1993 | Landis | |
| 5,331,691 A | 7/1994 | Runckel | |
| 5,334,646 A | 8/1994 | Chen | |
| 5,343,878 A | 9/1994 | Scarberry et al. | |
| 5,349,949 A | 9/1994 | Schegerin | |
| 5,390,373 A | 2/1995 | Flory | |
| 5,400,781 A | 3/1995 | Davenport | |
| 5,429,683 A | 7/1995 | Le Mitouard | |
| 5,477,852 A | 12/1995 | Landis et al. | |
| 5,485,837 A | 1/1996 | Soles Bee et al. | |
| 5,511,541 A | 4/1996 | Dearstine | |
| 5,517,986 A * | 5/1996 | Starr et al. | 128/206.24 |
| 5,522,382 A | 6/1996 | Sullivan et al. | |
| 5,540,223 A | 7/1996 | Starr et al. | |
| RE35,339 E | 10/1996 | Rapoport | |
| 5,560,354 A | 10/1996 | Berthon-Jones et al. | |
| 5,570,684 A | 11/1996 | Behr | |
| 5,592,938 A | 1/1997 | Scarberry et al. | |
| 5,617,849 A | 4/1997 | Springett et al. | |
| 5,645,054 A | 7/1997 | Cotner et al. | |
| 5,647,357 A * | 7/1997 | Barnett et al. | 128/206.24 |
| 5,657,752 A | 8/1997 | Landis et al. | |
| 5,660,174 A | 8/1997 | Jacobelli | |
| 5,662,101 A | 9/1997 | Ogden et al. | |
| D385,960 S | 11/1997 | Rudolph | |
| 5,704,345 A | 1/1998 | Berthon-Jones | |
| 5,724,964 A * | 3/1998 | Brunson et al. | 128/205.27 |
| 5,740,795 A | 4/1998 | Brydon | |
| 5,746,201 A | 5/1998 | Kidd | |
| D398,987 S | 9/1998 | Cotner et al. | |
| D402,755 S | 12/1998 | Kwok | |
| RE36,165 E | 3/1999 | Behr | |
| 5,884,624 A | 3/1999 | Barnett et al. | |
| 5,896,857 A | 4/1999 | Hely et al. | |
| 5,966,745 A | 10/1999 | Schwartz et al. | |
| 6,006,748 A | 12/1999 | Hollis | |
| D419,658 S | 1/2000 | Matchett et al. | |
| D421,298 S | 2/2000 | Kenyon et al. | |
| 6,019,101 A | 2/2000 | Cotner et al. | |
| 6,029,660 A | 2/2000 | Calluaud et al. | |
| 6,029,665 A | 2/2000 | Berthon-Jones | |
| D423,096 S | 4/2000 | Kwok | |
| 6,044,844 A | 4/2000 | Kwok et al. | |
| 6,091,973 A | 7/2000 | Colla et al. | |
| D428,987 S | 8/2000 | Kwok | |
| 6,098,205 A | 8/2000 | Schwartz et al. | |
| 6,112,746 A | 9/2000 | Kwok et al. | |
| 6,152,137 A | 11/2000 | Schwartz et al. | |
| 6,397,847 B1 * | 6/2002 | Scarberry et al. | 128/206.24 |
| 6,513,526 B2 * | 2/2003 | Kwok et al. | 128/206.24 |

OTHER PUBLICATIONS

Parker Laboratories, Inc., Aquaflex® Ultrasound Gel Pad sales literature, 1991, 1 page.

3M Health Care sales brochure, *Just plain talk about the many uses of Tegaderm™ transparent dressing*, 1990, 12 pages.

Lifecare® Form #544, 1 page, dated Jul. 1991.

ResCare Sullivan® Bubble Mask™ System Series 3 advertisement, 3 pages, undated.

Respironics Inc. Monarch Mini Mask information sheet, 1 page, dated Feb. 26, 1996.

Respironics Inc. Pamphlet, "Profile™ Custom Nasal Mask Instructions for Use," Dec. 14, 1998.

Smith et al., "Indications and Standards for Use of Nasal Continuous Positive Airway Pressure (CPAP) in Sleep Apnea Syndromes," Am. J. Respir. Crit. Care Med. 150:1738–45 (1994).

Vital Signs, Inc. Pamphlet, "SoftNair™" (1998).

* cited by examiner

FIG. 10A

AIR MASK WITH SEAL

TECHNICAL FIELD

The present invention relates to respiratory apparatus and more specifically to nasal masks useful for providing pressurized air or therapeutic gas to a patient suffering from an airflow limitation or other respiratory ailment.

BACKGROUND INFORMATION

Patients suffering from a variety of medical conditions often require supplementary respiratory support. Depending on the nature and severity of the condition, this respiratory support can range from providing an elevated oxygen concentration cloud to the vicinity of the nose and mouth, to forcing ventilation of the lungs by intubating the trachea. In general, a supply of pressurized air or therapeutic gas is provided by a tube or conduit to a delivery apparatus designed to conform to particular body structure.

One style of delivery apparatus is a mask which provides the gas to a nasal area of the patient. Nasal masks are often employed in the treatment of sleep apnea syndrome, characterized by intermittent upper airway obstruction during sleep. Due to the resulting blood oxygen desaturation and frequent arousals from sleep, persons suffering from this condition are often unable to achieve deep sleep for extended periods and are chronically tired and physically compromised.

Since nasal masks are often worn by persons in unmonitored environments for extended periods, such as in the home during sleep, the nasal mask should be comfortable to wear and conform well to the nasal area, thereby defining a substantially sealed chamber. If the mask is deemed too bulky, too heavy, or to fit poorly, the patient will either not wear the mask, wear the mask improperly, or only wear the mask occasionally when the discomfort associated with the respiratory condition exceeds the discomfort of wearing the mask.

One problem associated with nasal masks relates to the conformance of the mask to the nasal area, which is complexly contoured and differs from patient to patient. Customized masks manufactured to suit particular patients tend to be costly; therefore, masks for general use are typically made in several generic sizes, each size being designed to attempt to accommodate a range of patients. If the mask does not form a good seal around the patient's nose, leakage can occur, reducing the effectiveness of the treatment. When poorly fitting masks are used with variably regulated air supply systems responsive to patient breathing, such as those developed for treating sleep apnea, mask leakage can induce improper system response, which may exacerbate the patient's condition. Regulated air supply systems and delivery apparatus for treatment of sleep apnea are disclosed in Patent Cooperation Treaty international application number PCT/US93/05095, published on Dec. 9, 1993, as international publication number WO 93/24169; U.S. patent application Ser. No. 08/184,976 filed Jan. 24, 1994; U.S. Pat. No. 5,199,424; U.S. Pat. No. 5,245,995; U.S. Pat. No. 5,522,382; U.S. patent application Ser. No. 08/741,524 filed Oct. 31, 1996; U.S. Pat. No. 5,645,054; and U.S. Des. Pat. No. D398,987, the disclosures of all of which are herein incorporated by reference.

One method of reducing leakage is to provide a compliant sealing flange or surface around a perimeter of the mask in combination with a strap to bias the mask into sealing engagement with the contour of the nasal area of the patient. Typically, the greater the retention force applied by the strap, the better the seal; however, both the strap and the mask can cause excessive pressure on delicate areas resulting in irritation and patient discomfort.

The retention force required to prevent leakage is also a function of forces and torques induced in the mask. For example, the weight of the conduit supplying air or gas to the mask tends to pull the mask downward, away from the patient's nasal area, when the patient is sitting. Additionally, any movement of the head from side-to-side or up and down can cause lifting of an edge or sliding of the mask and strap. The more rapid the movement, the more pronounced the effect. Mask slippage and displacement are exacerbated in masks employing large diameter, heavy, or stiff tubes which deliver relatively large volumetric flow rates of air, such as those employed in sleep apnea treatment systems.

For nasal masks used by patients when sleeping, the strap and seal arrangement should also accommodate unconscious or reflexive head and body movements. The discomfort associated with masks which apply too much pressure to the head, neck, or nasal area discourage use of the mask during sleep when it is most needed. As a result, treatment is compromised and the patient is ill served by the apparatus.

Accordingly, there exists a need to overcome the limitations of known designs by providing an improved nasal mask which provides a consistent, reliable nasal area seal while being comfortable to wear. Other desirable features include ease of manufacture and low cost.

SUMMARY OF THE INVENTION

The present invention provides a nasal mask which is both comfortable for a user and seals reliably over a user's nasal area. More particularly, the present invention includes a comfortable soft seal affixed to a flexible shell. This soft seal both promotes a comfortable fit of the nasal mask on a user and a reliable seal between the nasal mask and a user's facial skin.

The design of nasal masks according to the invention provides solutions to several common problems with conventional designs. For example, the nasal mask's seal distributes contact pressure, unlike many current masks. Also, the design allows the user to comfortably lie in almost any position and to shift positions, either voluntarily or involuntarily, without disturbing the sealing engagement between the nasal mask and user's face. Additionally, the design provides for a nasal mask of single size that gives a comfortable fit and a reliable seal for a large segment of the population, in contrast to many current masks which either must be stocked in multiple sizes or which simply do not properly fit on users with faces of certain shapes.

According to one aspect of the invention, a nasal mask includes a flexible shell and a seal. The flexible shell contains an inlet and a malleable element disposed about a periphery of the shell for maintaining the shell in a selectable configuration. The seal is disposed along a perimeter of the shell so as to form a chamber within the shell when the mask is donned by a user.

Certain embodiments of this aspect of the invention may include any or all of the following features. The seal can be a thin bladder filled with a very low durometer silicone gel which is molded in a predetermined configuration. The seal may be bonded to the shell or otherwise maintained in sealing relation with the shell.

Some embodiments of the nasal mask can include a conduit attached to the inlet. The conduit may include an angled portion, a rotary connection, and/or a ball and socket connection. Also, the conduit can have one or more openings in a side wall thereof, to provide venting of flow passing through a lumen formed by the side wall of the conduit.

Additionally, some embodiments of the nasal mask can include a headgear apparatus attached to the mask for retaining the mask on a user. The nasal mask may include a retainer disposed about the inlet and cooperating with the headgear apparatus to retain the mask comfortably and reliably on a user. The headgear apparatus can include at least one connector for attaching the headgear apparatus to the mask, the connector being attached permanently or releaseably to the retainer.

According to another aspect of the invention, a system for treating a respiratory ailment in a recumbent or sleeping user includes a mask as described above in communication with a controlled, breathable gas source via a conduit.

According to still another aspect of the invention, a seal for use with a nasal mask includes a bladder having a first surface manufactured from a film of a certain thickness and a second surface manufactured of a thinner film. The bladder can be filled with a material, such as a silicone gel, having a durometer value of less than about ten on a Shore OOO scale. Additionally, when manufactured, one surface of the bladder can be substantially planar.

BRIEF DESCRIPTION OF THE DRAWINGS

The invention, in accordance with preferred and exemplary embodiments, together with further advantages thereof, is more particularly described in the following detailed description, taken in conjunction with the accompanying drawings.

In the drawings, like reference characters generally refer to the same parts throughout the different views. Also, the drawings are not necessarily to scale, emphasis instead generally being placed upon illustrating principles of the invention.

DESCRIPTION

The present invention provides a comfortable, reliably sealing nasal mask for delivering a breathable gas to a user. In particular a seal bonded to a shell of the nasal mask is particularly soft, having a very low durometer for conforming comfortably about the nasal area of a user. Nasal masks according to the invention, for example, but without limitation, are useful for treating respiratory ailments in a recumbent or sleeping user.

Embodiments of the present invention provide nasal masks that not only ergonomically perform better than current designs in delivering breathable gas to a sleeping or recumbent user, but also provide increased comfort for the user. Embodiments of the present invention are designed with a proper deformable, compliant, and resilient configuration for fitting over a user's nasal area. The mask includes a very soft seal which is comfortable against a user's skin and which is contoured in an ergonomic fashion in order to both seal reliably against a user's skin and fit comfortably against the skin. Furthermore, the headgear, which retains the mask on the user, in combination with the design of the conduit allows a user to wear comfortably such a nasal mask while sleeping in a variety of positions.

Figure 1:
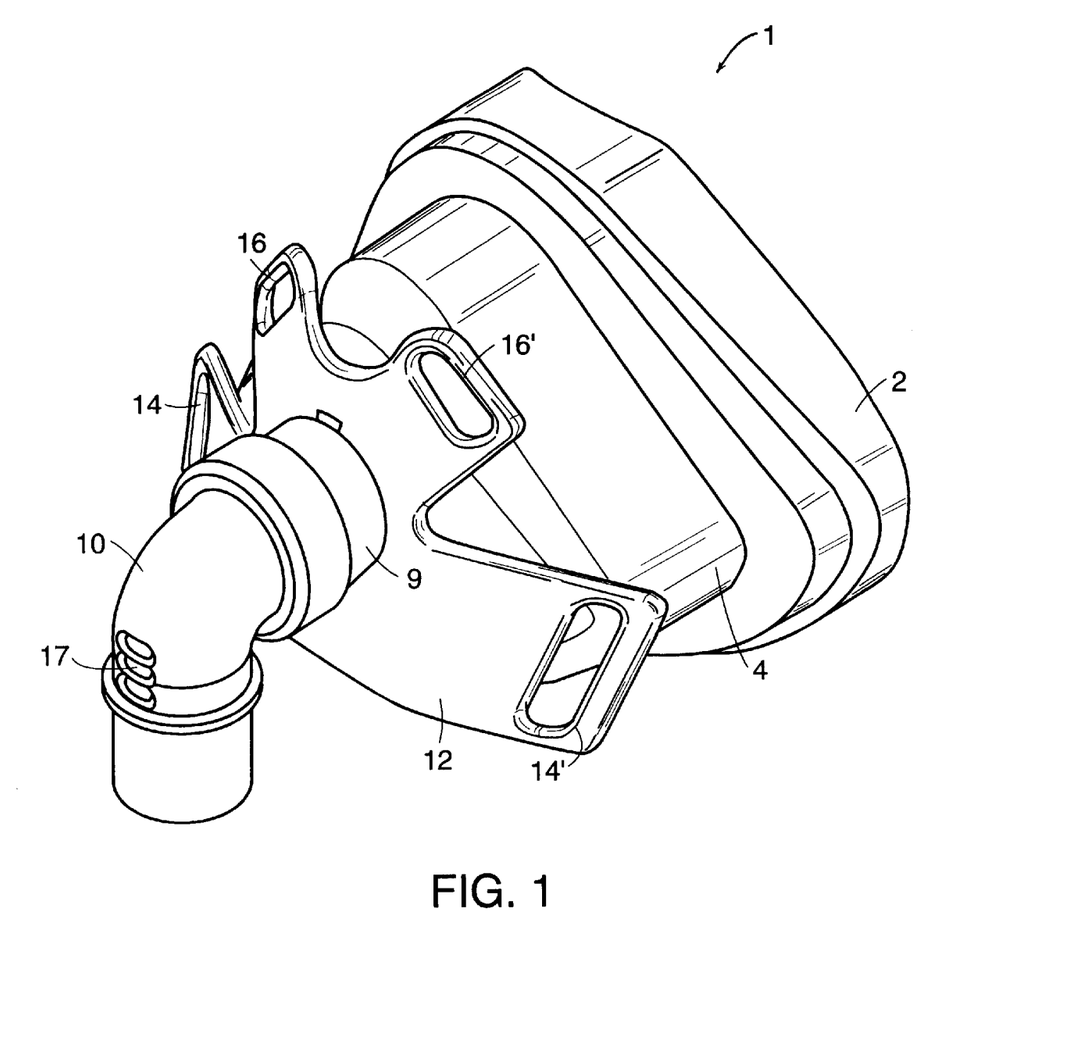
FIG. 1 is a schematic perspective view of a nasal mask according to one embodiment of the invention.
Figure 2A:
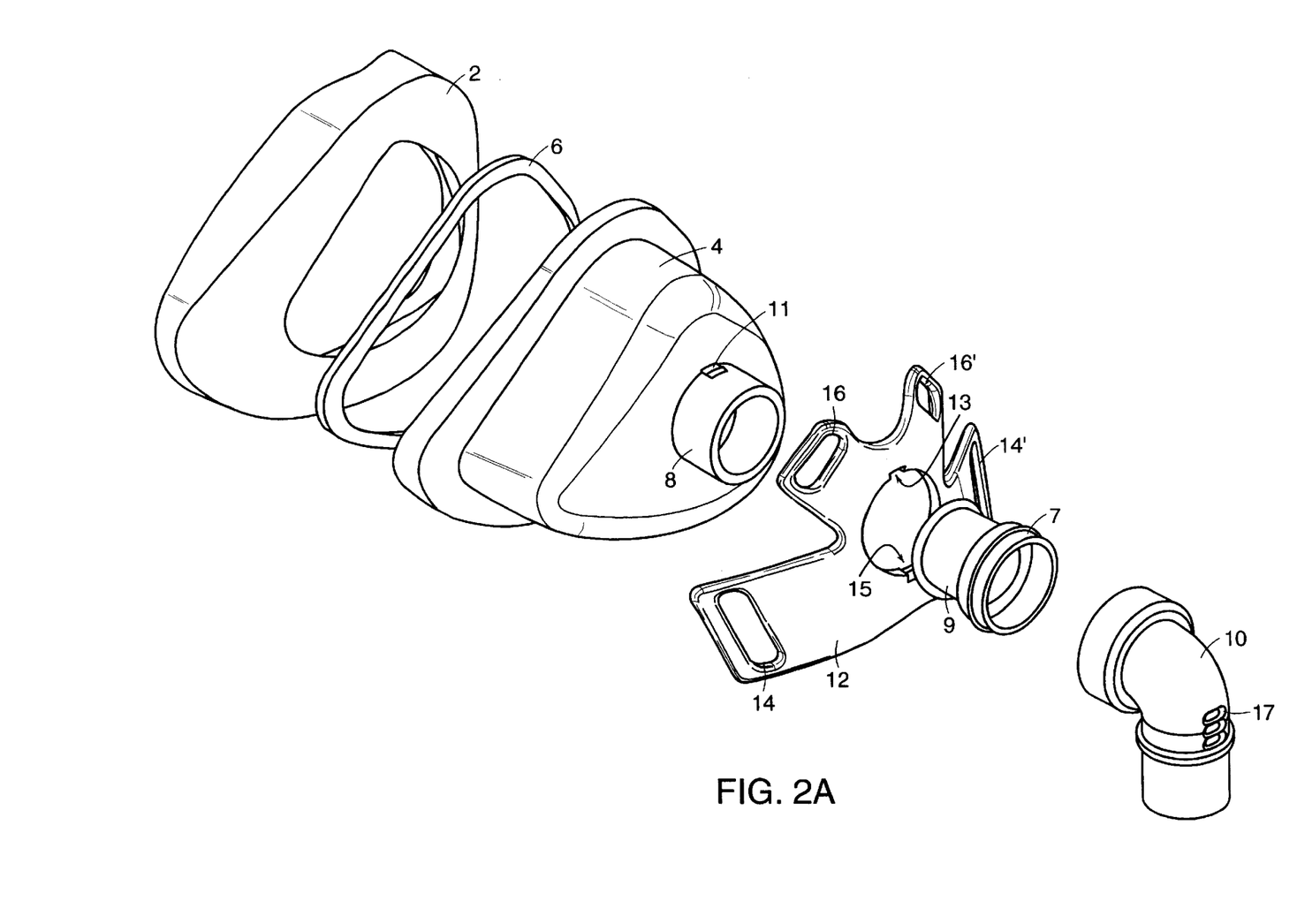
FIG. 2A is a schematic exploded perspective view of the components of the nasal mask depicted in FIG. 1.
Figure 2B:
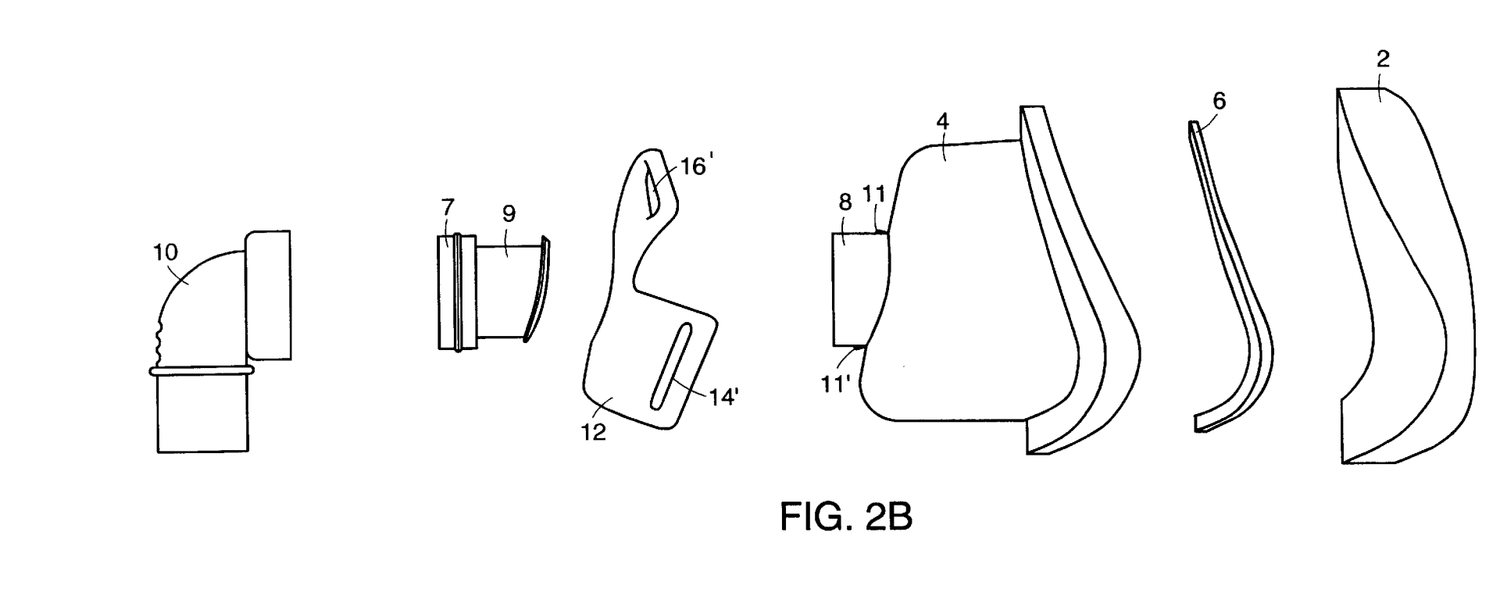
FIG. 2B is a schematic exploded side view of the components of the nasal mask depicted in FIG.
Figure 2C:
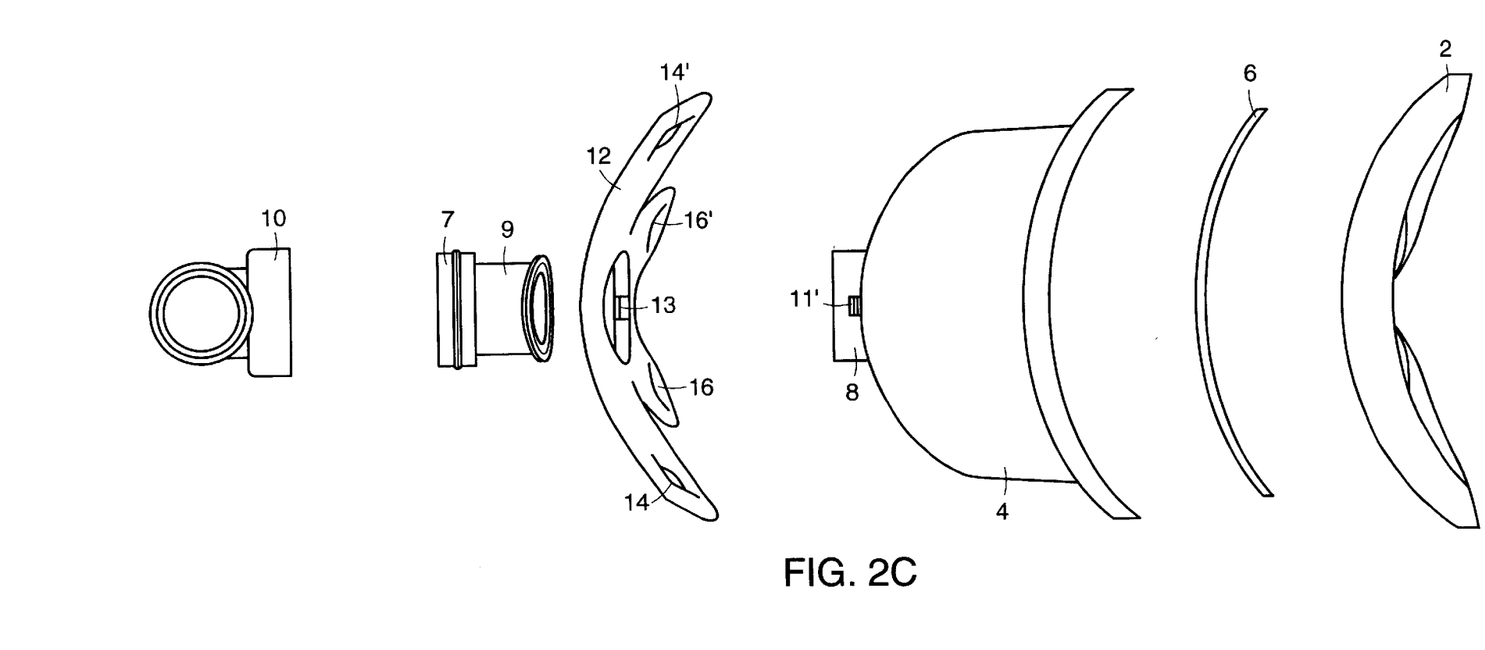
FIG. 2C is a schematic exploded bottom view of the components of the nasal mask depicted in FIG. 1.
Figure 3:
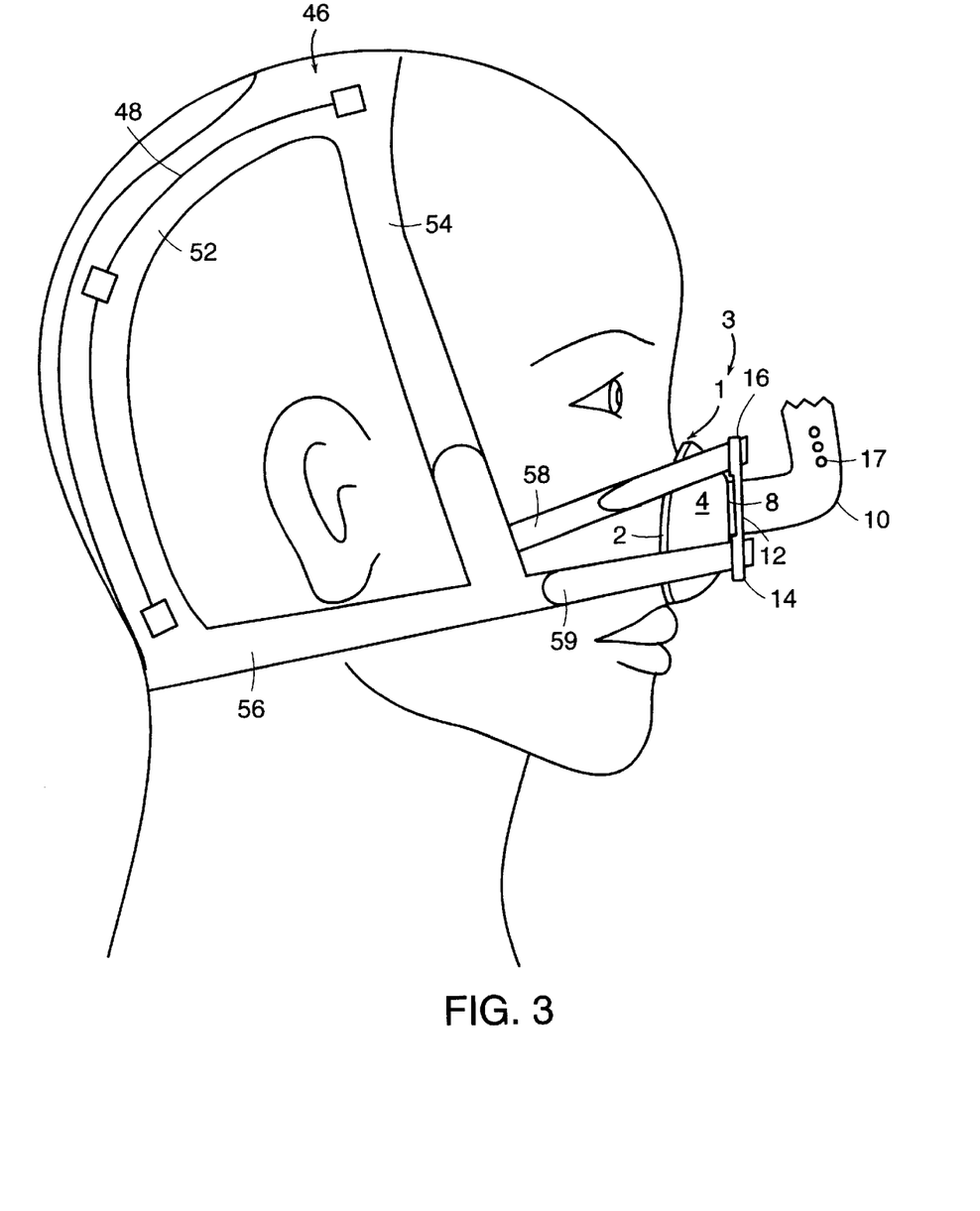
FIG. 3 depicts one embodiment of a nasal mask in accordance with the invention being donned by a user.
Figure 8:
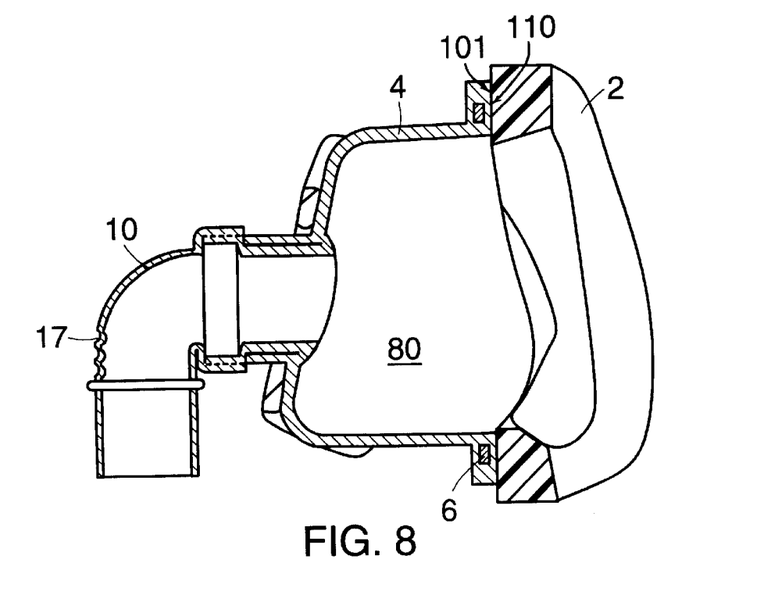
FIG. 8 is a schematic sectional view of the nasal mask of FIG. 7 taken along line A—A.

Referring to FIGS. 1 and 2, one embodiment of a nasal mask 1 according to the invention includes a seal 2 affixed to a shell 4, for example by bonding. Alternatively, other attachment methods may be employed to affix the seal 2 and provide an airtight interface. For example, mechanically interlocking features, such as a tapered dovetail or flange, could be employed with mating recesses. The shell 4, typically is manufactured from a flexible material by a molding process using a compliant polymer. For example, but without limitation, one compliant material is Pellethane™ available from Dow Corning Corporation, Midland, MI. Other compliant polymer, thermopolymer elastomers, or vinyl materials and other processes may be employed. The shell 4 has a generally triangular shape that is convex and is contoured such that a chamber 80 is formed by the sides of the shell 4 for receiving therein a patient's nose, as best seen in FIGS. 3 and 8. When in fluidic communication with a source of breathable gas, the chamber 80 contains the breathable gas. The gas in the chamber 80 is available to the user donning the nasal mask 1, and the gas, typically, is pressurized such that the gas is forced in to the user's airway, holding open the airway. The chamber 80 is substantially leakage-free due to the bond or interface between the seal 2 and the shell 4, and the conformance of the seal 2 against a user's skin.

Disposed within a perimeter portion of the shell 4 is a malleable element 6, best seen in FIG. 8. In this embodiment, the malleable element 6 is a ring of a relatively soft metal, such as aluminum or copper, disposed about the opening of and within the shell 4. Alternatively, the malleable element 6 can be affixed to a surface of the shell 4. The malleable element 6 can be constructed from any material that is formable and is capable of retaining the shape into which it is formed against the force of, for example, the flexible shell 4 trying to regain its memory shape. The combination of the compliant and resilient shell 4 and the malleable element 6, having sufficient rigidity to hold the shell 4 in a selected configuration, produces a "custom-fit" as desired by a particular user. Because the shell 4 is compliant, the perimeter and overall configuration of the opening of shell 4 can be reformed repeatedly, as necessary, by a particular user.

The nasal mask 1 also forms an inlet 8 with which a swivel connector 9 or other connector for a conduit mates. The end of the swivel connector 9 that mates with the inlet 8 may be angled relative to a centerline of the inlet 8 and of the swivel connector 9, in order to match a slope of the shell 4 at the inlet 8, as best seen in FIG. 2B. A conduit elbow 10 fits onto the swivel connector 9 at a sealing flange 7 on the swivel connector 9. The connection between the inlet 8 and the swivel connector 9 and/or the connection between the swivel connector 9 and the conduit elbow 10 can be a permanent and inseparable connection or the connection can be a selectively removable connection. The swivel connector 9 produces a swivel mount connection between the conduit elbow 10 and the inlet 8. In this type of connection, the conduit elbow 10 is capable of rotating 360 degrees about the centerline of the inlet 8 and the connector 9. In an alternative embodiment, the connection may employ a ball and socket. In this alternative type of connection, the conduit elbow has a second angular degree of freedom in addition to the single rotational degree of freedom of the swivel mount connection. The conduit attached to the conduit elbow 10 may be manufactured from, for example, but without limitation to, a polycarbonate or a polyolefin elastomer in a corrugated configuration, available from Smoothbore Plastics, Laguna Hills, Calif. The swivel connector 9 and conduit elbow 10 also can be manufactured from, for example, but without limitation, a polycarbonate material.

The conduit elbow 10 is shown with an angled portion of about ninety degrees, as well as one or more apertures 17, only one aperture being labeled for clarity. These apertures 17 vent the pressurized chamber 80 in order to allow the release of gases exhaled by the user, as well as preferentially vent the chamber 80 upon overpressurization. In current hose designs a user can be disturbed by gasses escaping from the hose through the conduits because of noise or a "blowing" sensation. The apertures 17 of this embodiment of the invention are sized and located to prevent escaping gases from disturbing a user due to noise or impingement on the user's face. More than one aperture 17 may be used to diffuse the flow of exhaled and venting gas. Additionally, the apertures 17 may have smoothly contoured edges at their respective perimeters to prevent whistling of gas moving through the apertures 17. The apertures 17 are positioned along the outside of the conduit elbow 10 so that gas is released remotely from the user in a single direction, rather than toward the user or in multiple directions. Moreover, the nasal mask 1 can optionally include more than one inlet to allow for additional hoses and/or sources of therapeutic gas to be connected. Also, one or more outlets can be included, optionally, in a lower portion of the shell 4 to allow for drainage of any condensation formed within the chamber 80 of the shell 4 and/or to attach pressure, temperature, flow, or other monitoring devices.

Figure 7:
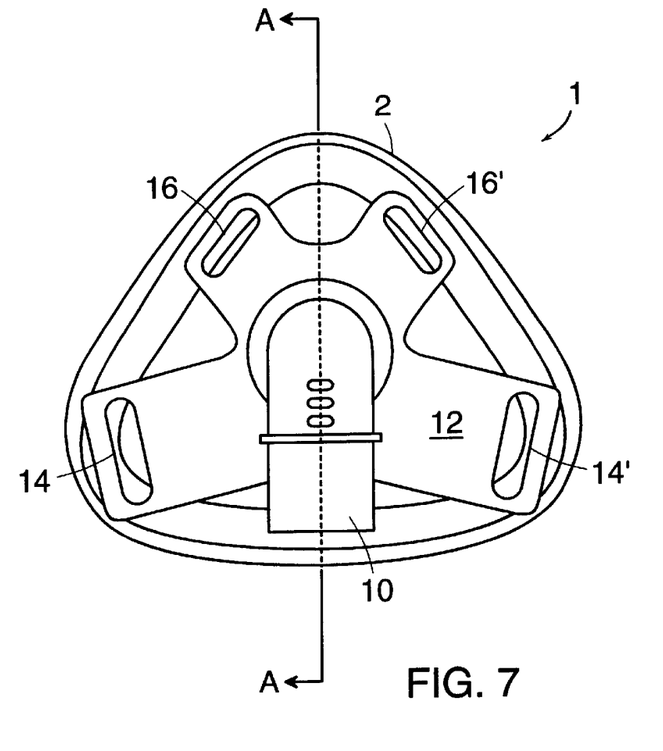
FIG. 7 is a schematic front view of the nasal mask of FIG. 1.

A retainer 12 is disposed about the inlet 8 to facilitate retention of the mask 1 on a user. The features of the retainer 12 of the nasal mask 1 are best illustrated in FIGS. 2A–2C. The retainer 12 is contoured such that it approximately matches the external curvature of the contoured shell 4. Two tabs 11, 11' included on the inlet 8 mate with two slots 13, 15 formed in the retainer 12 in a particular angular orientation. The retainer 12 has four connection points disposed remotely from the inlet 8, two lower connection points 14, 14' and two upper connection points 16, 16'. The nasal mask 1 is substantially symmetrical, as best seen in FIG. 7. Typically, the tabs 11, 11' hold the retainer 12 in an orientation such that the upper connection points 16, 16' are above the lower connection points 14, 14' and all connection points 14, 14', 16, 16' are disposed symmetrically about a vertical centerline A—A of the mask 1. These connection points 14, 14', 16, 16' form slots which allow for connection of the retainer 12 with straps of a headgear apparatus, as shown in FIG. 3. The retainer 12 can be constructed from, for example, but without limitation, a polycarbonate material. Of course, alternative embodiments may have a different number of connection points or may have a mechanically different method of fastening the headgear apparatus to the nasal mask 1. For example, snaps, hook and eye closures, hook and loop fasteners, or the like, may be employed.

Now referring to FIG. 3, when the nasal mask 1 is donned by a user, the nasal mask 1 is maintained in sealing relation with the user's nasal area with a headgear apparatus 46 to form a complete nasal mask assembly 3. The headgear apparatus 46 may include a plurality of straps 52, 54, 56 which circumscribe the head, as depicted in FIG. 3. The straps 52, 54, 56 of the headgear apparatus 46 are configured and oriented so as not to fall across the ears of a user. Avoiding contact between the straps 52, 54, 56 and the ears of a user increases the comfort level of a user wearing the headgear apparatus 46. The straps 52, 54, 56 may be manufactured from inelastic or elastic materials such as, but not limited to, nylon webbing, nylon covered neoprene or Velstretch™, available from Velcro USA Inc., Manchester, N.H., and may further include optional padding, if desired. The headgear apparatus 46 also can be reinforced with a beam element 48 that allows the headgear apparatus 46 to retain a roughly helmet shape when not placed on the head of a user. The beam element 48 may be plastically or elastically deformable and may be manufactured, for example, from a polymer, metal, or other suitable material. According to one embodiment, the beam element may have a substantially flat cross-section, so as not to create an uncomfortable ridge if rested upon. Maintaining the helmet shape allows a user to more easily don the headgear 46. Of course, those skilled in the art appreciate that other equivalent headgear apparatus configurations and headgear apparatus materials may be suitable.

The headgear apparatus 46 is connected to the retainer 12 disposed about the inlet 8. Specifically, the headgear apparatus 46 includes two upper retention straps 58 and two lower retention straps 59 (only one upper and one lower retention strap being shown, the others being hidden from view), each of which are attached to corresponding upper and lower connection points 16, 14, respectively.

This four point restraining system permits the nasal mask 1 to be securely and gently biased against a user's nasal area. The lower connection points 14, in concert with the lower retention straps 59, generally maintain the nasal mask 1 against a user's face. The upper connection points 16 in concert with the upper retention straps 59, provide additional retention force on the upper portion of the nasal mask 1, proximate a user's eyes, to ensure sealing along the bridge of the nose and prevent annoying air leaks which would impinge upon the user's eyes. The upper retention straps 59 are configured and oriented so as not to block the vision of a user. Additionally, the lower and upper connection points 14, 16 are disposed at different radial distances from the inlet 8, generally being aligned with the perimeter of the shell 4 to optimize biasing of the seal against the user's nasal area and routing of the headgear apparatus 46.

In use, a user loops each of the lower and upper retention straps 59, 58 through respective slots in each of the lower and upper connection points 14, 16. A hook and loop fastener system can be used to maintain the straps 59, 58 at a desired adjustment. The loops may be located along the majority of the lengths of the straps 59, 58 to provide a wide range of adjustment, with the hooks being located on the distal tip portions of the straps 59, 58, such that when the distal tip of a strap is passed through a slot in a connector, the strap folds over on itself and the hooks engage the loops. Alternatively, the correct length of a strap can be adjusted and a snap on the distal tip can engage with a mating button along the strap. Thus, a user only has to adjust a strap once, rather than adjusting the straps each time the user dons the nasal mask.

The properly adjusted retention straps 59, 58 of the headgear apparatus 46 ensure proper contact between the seal 2 of the nasal mask 1 and the user's skin in the nasal area. The additional force provided by the upper connection points 36 and the upper retention straps 59 ensures that the nasal mask 1 fits securely to a user's face during a wide range of sleeping behaviors such as entering and maintaining a preferred sleeping position or performing involuntary movements during sleep.

Still referring to FIG. 3, the conduit elbow 10, connected to the inlet 8, allows for gas from a breathable gas source to flow through the conduit elbow 10, past the apertures 17, and into the cavity 80 formed by the nasal mask 1. Loops of rigid or compliant material may be affixed to or captured by any of the straps 52, 54, 56 to support a supply conduit in fluidic communication with the conduit elbow 10.

Figure 4:
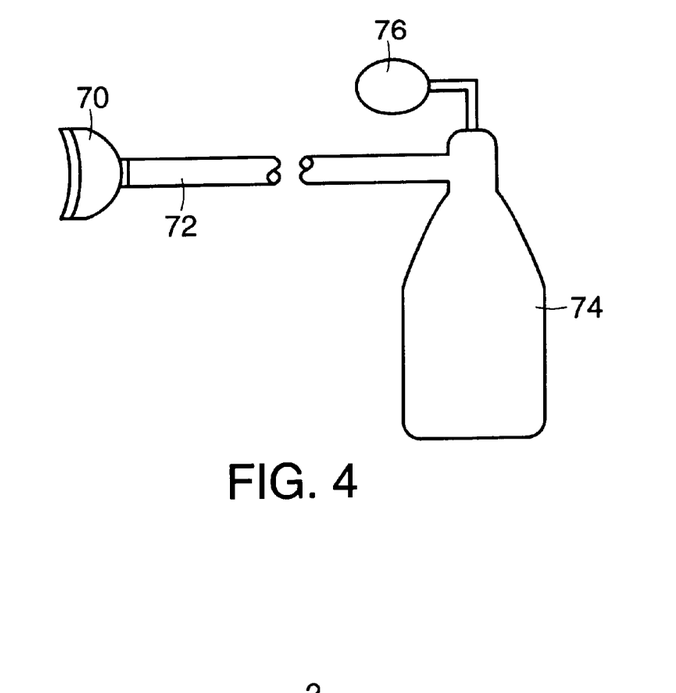
FIG. 4 is a schematic representation of a system for treating a respiratory ailment, the system including a breathable gas source in fluidic communication with a nasal mask.

Referring now to FIG. 4, an entire respiratory assistance system is depicted in which a breathable gas source 74 is connected to the nasal mask 1 by a supply conduit 72, the gas source typically being controlled by a controller unit 76. The breathable gas source 74 could be any of a ad variety of types and configurations, including, but not limited to, a constant flow air pump, a responsive variable flow air pump, a pressure regulated oxygen tank, or the like, as discussed in the references cited hereinabove.

Figure 5:
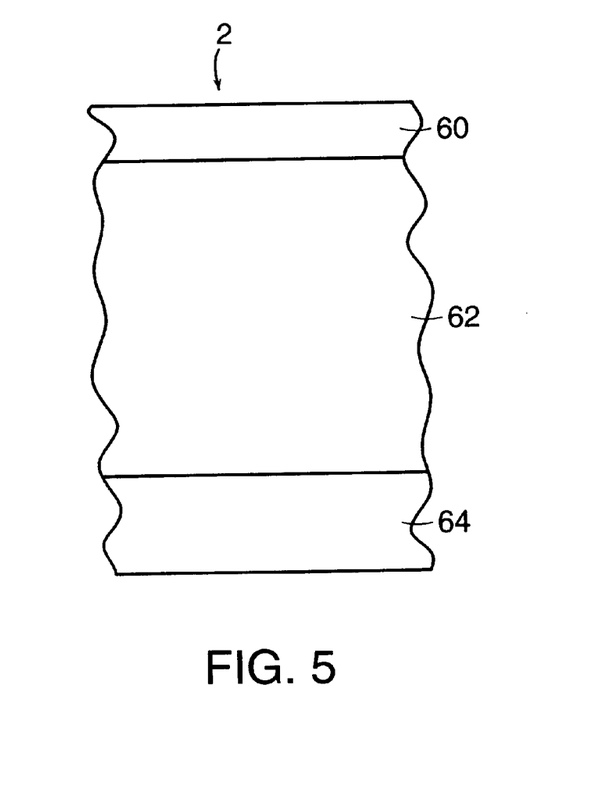
FIG. 5 depicts a schematic sectioned view through one embodiment of a seal in accordance with the present invention.
Figure 6A:
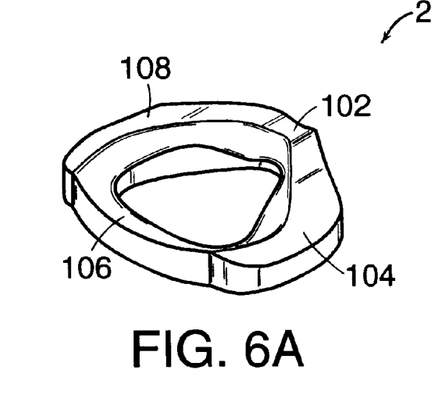
FIG. 6A is a schematic perspective view of another embodiment of a seal in accordance with the present invention.
Figure 6B:
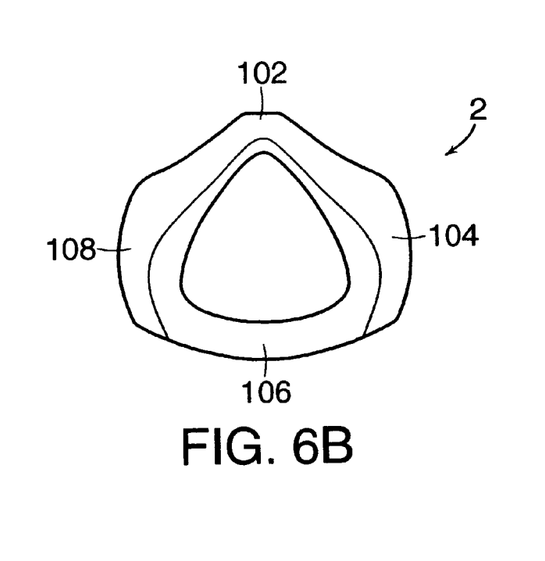
FIG. 6B is a plan view of a portion of the seal depicted in FIG. 6A that contacts a user's nasal area.
Figure 6C:
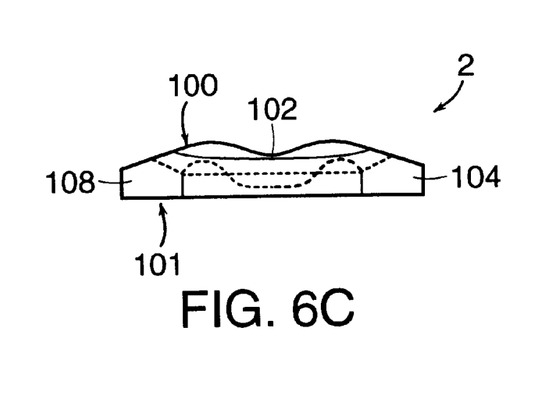
FIG. 6C depicts a schematic end view of the seal of FIG. 6A in the general orientation of FIG. 6B.
Figure 6D:
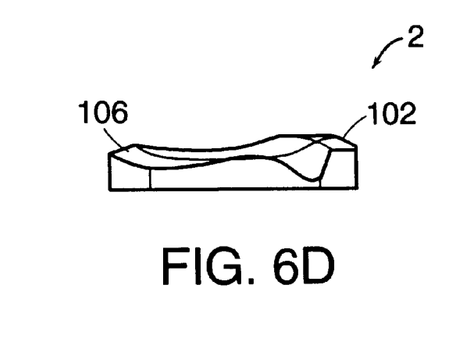
FIG. 6D depicts a schematic side view of the seal of FIG. 6A.

Now referring to FIG. 5, a section through the seal 2 is shown. Typically, the seal 2 is a bladder that is formed from a film 60, 64 and that is filled with a soft material 62. According to one embodiment, the fill material 62 has a durometer value of less than about ten on the Shore OOO scale so as to readily resiliently and compliantly conform to the nasal area of the user, without excessive force. For example, certain types of silicone gel meet this durometer value, such as, but not limited to, molded silicone commercially available from Bragel, Inc., Pomona, Calif., as a finished product, or as chemical silicone constituents, such as a base and a cross-link, that combine to form, when cured, such a finished product, such as those available from Applied Silicone Corporation, Ventura, Calif.

As stated hereinabove, according to one embodiment, the seal fill material has a durometer value of less than about ten on the Shore or Type OOO scale. Such low durometer values on this scale can be measured using apparatus and test methodology generally in accordance with Type A, B, C, D, DO, O, OO durometer test method of American Society for Testing and Materials (ASTM) Designation D 2240-97[e1]: Standard Test Method for Rubber Property—Durometer Hardness, approved Feb. 10, 1997, and revised editorially in February 1999. As is known by those skilled in the art of testing the durometer of ultrasoft gels and sponge rubber on the Shore OOO scale, a 0.5 inch hemispherical end indentor shape is used in combination with a 113 gram-force main spring.

According to this test method, the procedure for obtaining measurements of a specimen's durometer is stated as follows:

Place the specimen on a hard, horizontal surface. Hold the durometer in a vertical position with the point of the indentor at least 12 mm (0.5 in.) from any edge of the specimen, unless it is known that identical results are obtained when measurements are made with the indentor at a lesser distance. Apply the presser foot to the specimen as rapidly as possible, without shock, keeping the foot parallel to the surface of the specimen. Apply just sufficient pressure to obtain firm contact between presser foot and specimen.

When the durometer measurement is made as stated, while maintaining sufficient pressure to maintain contact, but without permitting the presser foot of the measuring apparatus to compress the silicone gel specimen, thereby forcing a portion of the specimen into the aperture formed about the indentor and binding the indentor, reliable, repeatable readings on the Shore OOO scale can be recorded.

Furthermore, the aforementioned test method states:

NOTE 9—The type of durometer should be selected with the knowledge that readings below 10 or above 90 are not considered reliable by the manufacturer. It is suggested that readings in these ranges not be recorded.

Although readings below 10 on the Shore scale are not considered reliable by ASTM, the Shore OOO scale is the lowest scale for durometer by Shore readings. In effect, the aforementioned seal fill material is too soft for measurement by ASTM approved Shore durometer test methods. However, a reference of below ten on the Shore OOO scale measured as described hereinabove is Applicant's preferred method for characterization of the seal softness in accordance with the invention. Further, this methodology is generally known by those skilled in the art and represents industry accepted measurement standards.

The bladder itself, typically, is made from a thermopolymer material. The bladder can be formed from, for example, but not limited to, a urethane film or a polyurethane film. Urethane films are commercially available, for example, from Deerfield Urethane, Inc., Deerfield, Mass., and polyurethane films are commercially available, for example, from Elf Atochem S.A. Paris, France. The film forming the bladder can be thicker in some portions relative to other portions. For example, FIG. 5 depicts a relatively thinner portion of the film 60 and a relatively thicker portion of the film 64. Typically, the film on the side of the seal 2 that is bonded to the shell 64 is thicker than the film on the side of the seal 2 which contacts the face of a user 60. In one embodiment, the seal 2 initially has about a 75 $\mu$m thick urethane film on the side bonded to the shell and has about a 50 $\mu$m thick urethane film on the side which contacts the face of a user. Accordingly, when the seal 2 is bonded to the shell 4, for example with a bonding agent such as tetrahydrofuran or an ultraviolet cured adhesive, sufficient margin exists to prevent the film from being breached due to attack by the bonding agent. The film disposed against the user's skin, however, is maintained relatively thin so as not to stiffen the seal 2.

FIGS. 6A–6D shows one configuration of the seal 2, as manufactured, with a perimeter having a generally contoured side 100 and a generally planar side 101. Typically, the contoured side 100 contacts a user's skin while the planar side 101 is affixed to the shell 4. The seal 2 includes four primary sealing areas: a nose bridge sealing portion 102, an upper lip sealing portion 106, and two side cheek sealing portions 104, 108. The side portions 104, 108 are about 0.35 inches thick, but vary in thickness depending upon the exact point of measurement due to the contouring of the seal 2. Each of these side portions 104, 108 contacts skin on either side of a user's nose, proximate the cheeks. The nose bridge portion 102 is about 0.46 inches thick, again, varying in thickness depending upon the exact point of measurement due to the contouring of the seal 2 and has a generally rectangular section with an arc removed from the contoured side that is Us about 0.5 inches wide, to better conform the seal 2 across the bridge of a user's nose. The upper lip portion 106 is about 0.4 inches thick and seals against the skin above a user's upper lip and below the nostrils, the upper lip portion varying in thickness, depending upon the exact point of measurement due to the contouring of the seal 2.

By configuring the seal 2 with a generally planar side 101, the seal 2 can be more readily manufactured than a seal which is complexly contoured throughout, because the seal mold can be a plate with a contoured cavity mated with a generally planar plate. Additionally, modification of the contoured side 100 of the seal 2 is more easily achieved, for example, but without limitation, by modifying solely the contoured cavity in the mold. Also, affixing the seal 2 to the shell 4 is readily accomplished, because both the shell perimeter 110 and the planar side 101 of the seal can be reliably mated and bonded, without concern for misalignment, nesting errors, or wrinkling which would result in unacceptable leakage between the seal 2 and the shell 4.

Figure 9:
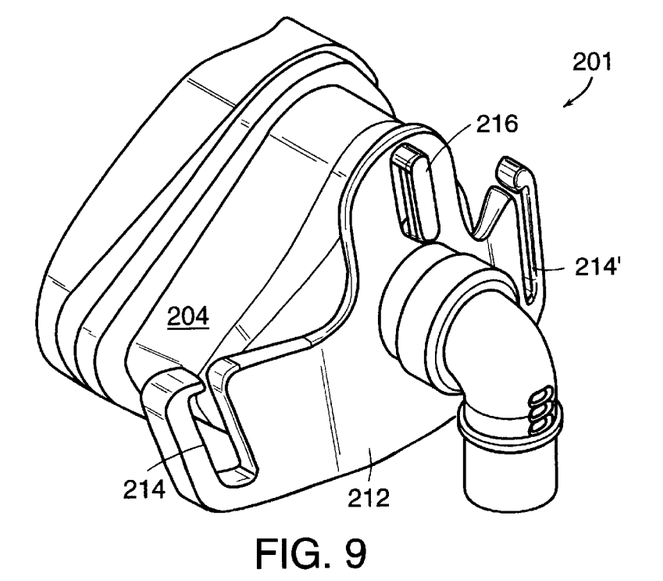
FIG. 9 is a schematic perspective view of a nasal mask according to an alternative embodiment of the invention.
Figure 10A:
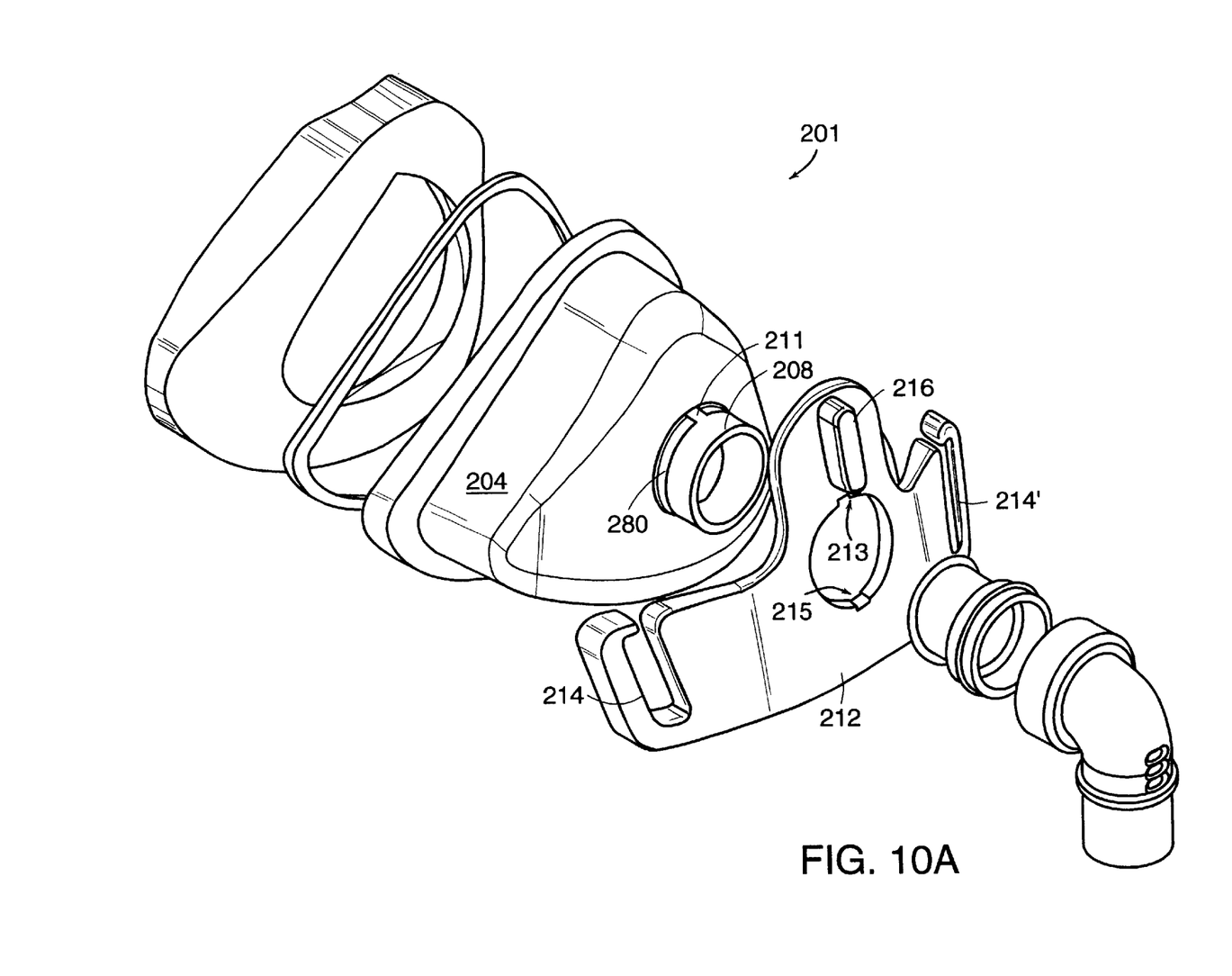
FIG. 10A is a schematic exploded perspective view of the components of the nasal mask depicted in FIG. 9.
Figure 10B:
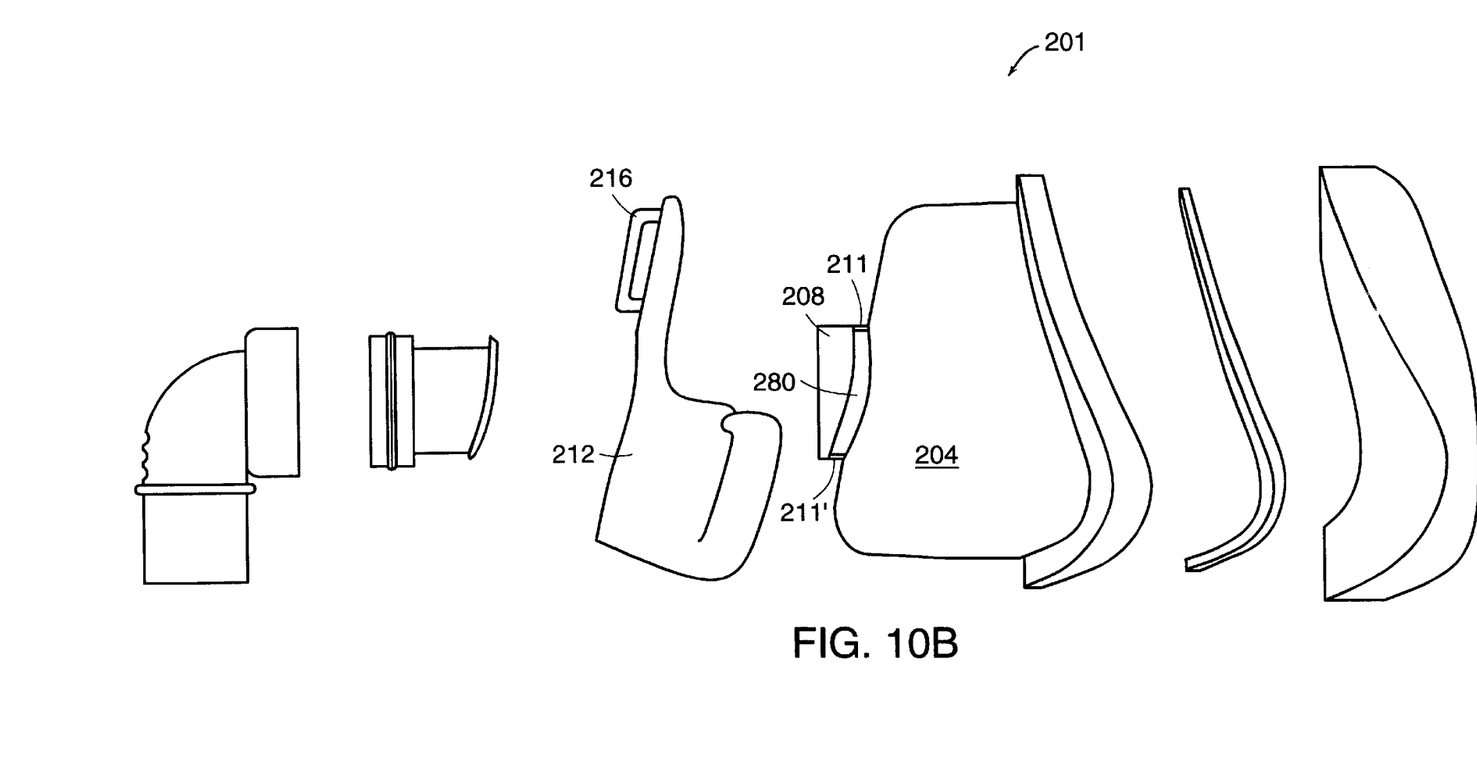
FIG. 10B is a schematic exploded side view of the components of the nasal mask depicted in FIG. 9.
Figure 11:
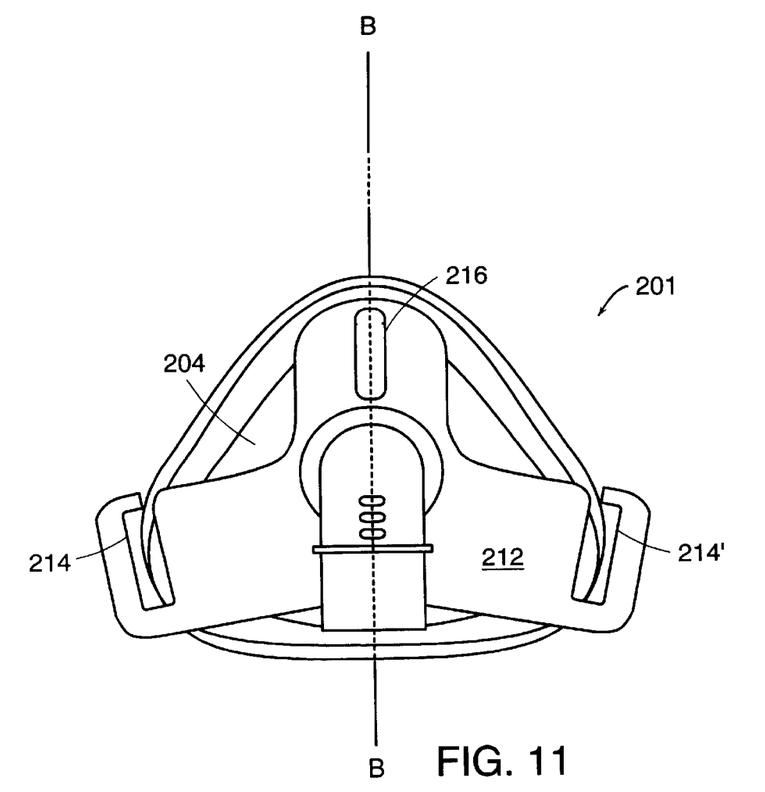
FIG. 11 is a schematic front view of the nasal mask of FIG. 9.

Now referring to FIGS. 9–11, an alternative embodiment of a nasal mask 201 has many, but not all, of the features of the nasal mask 1 embodiment shown in FIGS. 1–8. Two differences between this alternative nasal mask 201 embodiment and the nasal mask 1 embodiment shown in FIGS. 1–8 are, respectively, that a retainer 212 connects to an inlet 208 in a different manner than the retainer 12 connects to the inlet 8 and that the retainer 212 is configured differently than the retainer 12.

The retainer 212 is disposed about the inlet 208 to facilitate retention of the mask 201 on a user. The retainer 212 is contoured such that it approximately matches the external curvature of the contoured shell 204. Two tabs 211, 211' included on the inlet 208 mate with two slots 213, 215 formed in the retainer 212 in a particular angular orientation. The retainer 212 has three connection points disposed remotely from the inlet 208, two lower connection points 214, 214' and one upper connection point 216. The nasal mask 201 is substantially symmetrical, as best seen in FIG. 11. Typically, the tabs 211, 211' hold the retainer 212 in an orientation such that the upper connection point 216 is above the lower connection points 214, 214' and all connection points 214, 214', 216, are disposed symmetrically about a vertical centerline B—B of the mask 201. Also, a depressed annular region 280 on the inlet 208 mates with the edges of an aperture passing through the retainer 212. The retainer aperture and the inlet 208 are generally sized in an interference fit so that the retainer 212 is properly retained by the cooperation of the tabs 211, 211', the slots 213, 215, and the depressed annular region 280 when fully seated against the shell 204. The depressed annular region 280 does not completely encircle the inlet 208, thus forming the two tabs 211, 211'. The retainer 212 can be constructed from, for example, but without limitation, a polycarbonate material.

The connection points 214, 214', 216 form slots which allow for connection of the retainer 212 with straps of a headgear apparatus below. A three point restraining system permits the nasal mask 201 to be securely and gently biased against a user's nasal area. The lower connection points 214, 214' in concert with retention straps, generally maintain the nasal mask 201 against a user's face. The upper connection point 216 in concert with an upper retention strap provides additional retention force on the upper portion of the nasal mask 201, proximate a user's eyes, to ensure sealing along the bridge of the nose and prevent annoying air leaks which would impinge upon the user's eyes. The upper retention strap passes slidably through the upper connection point 216, best seen in FIG. 10B, and this single strap connects to other portions of a headgear apparatus. The upper retention strap is configured and oriented so as not to block the vision of a user. Additionally, the lower and upper connection points 214, 214', 216 are disposed at different radial distances from the inlet 208, generally being aligned with the perimeter of the shell 204 to optimize biasing of the seal against the user's nasal area and routing of a headgear apparatus.

In use, a user loops each of the lower retention straps through respective slots in each of the lower connection points 214, 214'. A hook and loop fastener system can be used to maintain the straps at a desired adjustment. The loops may be located along the majority of the lengths of the straps to provide a wide range of adjustment, with the hooks being located on the distal tip portions of the straps, such that when the distal tip of a strap is passed through a slot in a connector, the strap folds over on itself and the hooks engage the loops. Once the straps were adjusted, a user can slip the pre-formed loop into and out of the lower connection points 214, 214' at a notch that is cut into an edge of each of the lower connections points 214, 214'. The notch typically is removed from a portion of the lower connection points 214, 214' towards the centerline of the nasal mask 201 (line B—B in FIG. 11). Removing a notch from this portion allows the straps to be engaged and disengaged with the retainer 212 easily, while at the same time minimizes the possibility that the straps will slip out of their respective lower connection points 214, 214' while the nasal mask 201 is in use. Further, once the straps are adjusted a first time, they need not be adjusted again, merely being slipped out of the lower connection points 214, 214' by the notches.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A seal for use with nasal mask, the seal comprising a bladder having a first surface comprised of a first film and a second surface comprised of a second film, the first film being thicker than the second film and the bladder being filled with a soft material having a durometer value of less than about ten on a Shore OOO scale.

2. The seal of claim 1 wherein at least one surface of the bladder is substantially planar.

3. The seal of claim 1 wherein the material comprises a molded silicone gel.

4. The seal of claim 1 wherein the first film comprises a urethane film.

5. The seal of claim 1 wherein the first film comprises a polyurethane film.

6. The seal of claim 1 wherein the first film is about 75 µm thick.

7. The seal of claim 1 wherein the second film comprises a urethane film.

8. The seal of claim 1 wherein the second film comprises a polyurethane film.

9. The seal of claim 1 wherein the second film is about 50 µm thick.

10. The seal of claim 1 wherein at least one surface of the bladder is generally contoured.

11. The seal of claim 1 wherein the seal comprises a variable thickness.

12. The seal of claim 1 wherein a portion of the seal is between about 0.35 inches and about 0.46 inches thick.

13. A nasal mask comprising:

a shell; and a seal along a perimeter of the shell, wherein the seal comprises a bladder having a first surface comprised of a first film and a second surface comprised of a second film, the first film being thicker than the second film and the bladder being filled with a soft material having a durometer value of less than about ten on a Shore OOO scale.

14. The nasal mask of claim 13 further comprising a headgear apparatus attached to the mask for retaining the mask on a user.

15. The nasal mask of claim 14 further comprising a beam element for retaining the headgear apparatus in a shape.

16. The nasal mask of claim 13 wherein the seal is bonded to the shell.

17. A system for treating a respiratory ailment in a recumbent or sleeping user comprising:

a mask comprising:

a shell; and a seal along a perimeter of the shell, wherein the seal comprises a bladder having a first surface comprised of a first film and a second surface comprised of a second film, the first film being thicker than the second film and the bladder being filled with a soft material having a durometer value of less than about ten on a Shore OOO scale;

a controlled, breathable gas source; and a conduit connecting the mask with the gas source.

* * * * *